United States Patent
Bowers et al.

(10) Patent No.: US 6,321,588 B1
(45) Date of Patent: Nov. 27, 2001

(54) CHEMICAL SENSOR ARRAY

(75) Inventors: William D. Bowers, Newport Beach; Frank Bahrami, Costa Mesa; John Tran, Huntington Beach, all of CA (US)

(73) Assignee: Femtometrics, Inc., Irvine, CA (US)

( * ) Notice: Subject to any disclaimer, the term of this patent is extended or adjusted under 35 U.S.C. 154(b) by 0 days.

(21) Appl. No.: 09/151,747

(22) Filed: Sep. 11, 1998

(51) Int. Cl.[7] .................... G01N 27/00; G01N 29/00; G01N 31/06

(52) U.S. Cl. ............... 73/24.01; 73/592; 73/335.02; 73/24.05; 73/61.49; 73/610; 73/626; 324/727; 422/88; 422/69

(58) Field of Search ................. 73/61.75, 61.49, 73/61.45, 61.42, 335.02, 24.05, 24.01, 592, 610, 626, 628, 23.34; 422/88, 69; 324/636, 727

(56) References Cited

U.S. PATENT DOCUMENTS

| | | | |
|---|---|---|---|
| 4,361,026 | * 11/1982 | Muller et al. | 73/23 |
| 4,617,830 | * 10/1986 | Pál et al. | 73/590 |
| 4,630,482 | * 12/1986 | Traina | 73/597 |
| 4,818,348 | * 4/1989 | Stetter | 204/1 T |
| 4,888,295 | * 12/1989 | Zaromb et al. | 436/161 |
| 4,895,017 | * 1/1990 | Pyke et al. | 73/23 |
| 5,076,094 | * 12/1991 | Frye et al. | 73/19.03 |
| 5,221,871 | * 6/1993 | Fuchs et al. | 310/313 R |
| 5,306,644 | * 4/1994 | Myerholty | 436/149 |
| 5,325,704 | * 7/1994 | Mavianni et al. | 73/24.06 |
| 5,406,829 | * 4/1995 | Ravel et al. | 73/24.01 |
| 5,465,608 | 11/1995 | Lokshin et al. | 73/24.01 |
| 5,469,369 | 11/1995 | Rose-Pehrsson et al. | 364/497 |
| 5,473,934 | * 12/1995 | Cobb | 73/61.49 |
| 5,476,002 | 12/1995 | Bowers et al. | 73/24.01 |
| 5,488,866 | 2/1996 | Ravel et al. | 73/579 |
| 5,661,226 | * 8/1997 | Bowers et al. | 73/24.01 |

FOREIGN PATENT DOCUMENTS

| | | |
|---|---|---|
| 0 676 638 | 10/1995 | (EP) . |
| 9-131335 | 5/1997 | (JP) . |

OTHER PUBLICATIONS

Acoustic TSMSAWFPWAPM Wave Microsensors. Jay W. Grate, Stephen J. Martin, Richard M. White, Reprinted from Anal. Chem. 1993, vol. 65, 940A–948A.

(List continued on next page.)

*Primary Examiner*—Hezron Williams
*Assistant Examiner*—David J. Wiggins
(74) *Attorney, Agent, or Firm*—Knobbe, Martens, Olson & Bear, LLP

(57) ABSTRACT

A device for detecting chemical substances includes a plurality of sensors arranged in an array. The sensors are connected to respective oscillator circuits which drive the sensors, and the oscillator circuits are coupled to a power multiplexer which provides the circuits with power according to a timing pattern such that not all of the oscillator circuits are activated at any one time. Preferably, only one oscillator circuit is activated at any given time. This multiplexing arrangement saves power and substantially eliminates cross talk between the oscillator circuits. The oscillator circuits are preferably application specific integrated circuits (ASICs), and the sensors are preferably surface acoustic wave (SAW) devices. In use, the SAW sensors are exposed to a gas, such as air, containing the chemical substance to be detected. Signals from the SAW sensors are analyzed to identify the chemical substance.

23 Claims, 3 Drawing Sheets

OTHER PUBLICATIONS

Smart Sensor System for Trace Organophosphorus and Organosulfur Vapor Detection Employing a Temperature-Controlled Array of Surface Acoustic Wave Sensors, Automated Sample Preconcentration and Pattern Recognition, Jay W. Grate, Susan L. Rose-Pehrsson, David L. Venezky, Mark Klusty and Hank Wohltjen, Anal. Chem. 1993, 65, 1868–1881.

Acoustic TSMSAWFPWAPM Wave Microsensors, Jay W. Grate, Stephen J. Martin, Richard M. White, Reprinted from Anal. Chem. 1993, vol. 65, 987A–996A.

Naeves, P. I., et al.: "A new generation of integrated electronic noses", Sensors And Acuators B, vol. 27, pp. 223–231, 1995.

Klinkhachorn, P., et al.: "A Microprocessor–Based Piezoelectric Quartz Microbalance System for Compound–Specific Detection", IEEE Instrumentation and Measurement Technology Conference, Washington, DC, pp. 146–149, Apr. 25–27, 1989.

Jenkins, T. J. et al.: "Evaluation of a Microsensor Fabricated Using VLSI Technology and Doped Phthalocyanines for Detecting Nitrogen Dioxide", Proceedings of the IEEE 1992 National Aerospace and Electronics Conference, NAECON 1992 (Cat. No. 92CH3158–3), Dayton, OH, vol. 1, pp. 72–78, May 18–22, 1992.

* cited by examiner

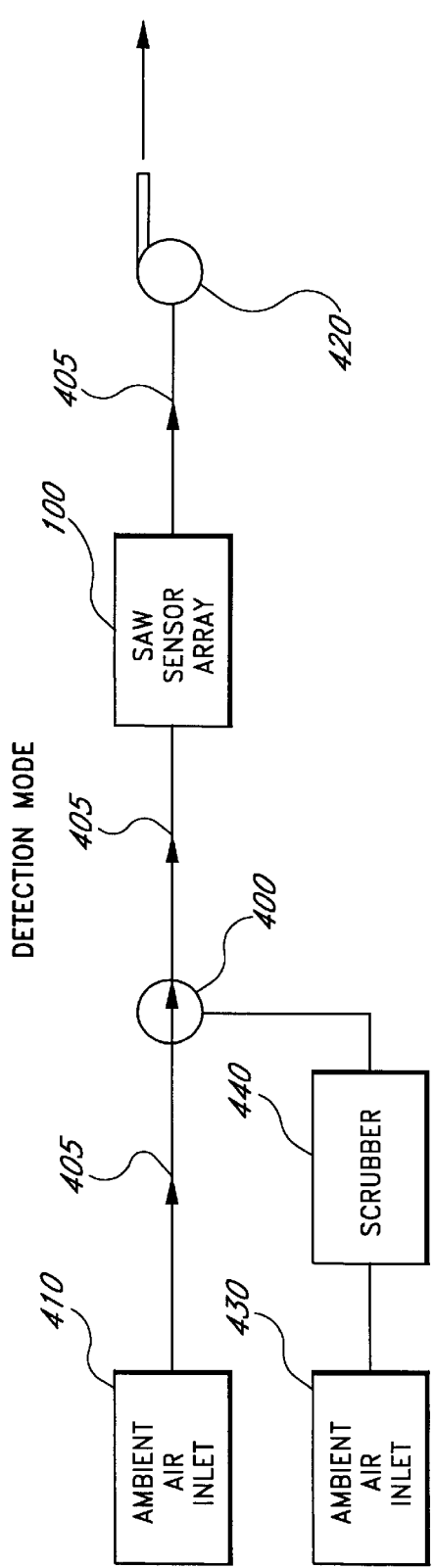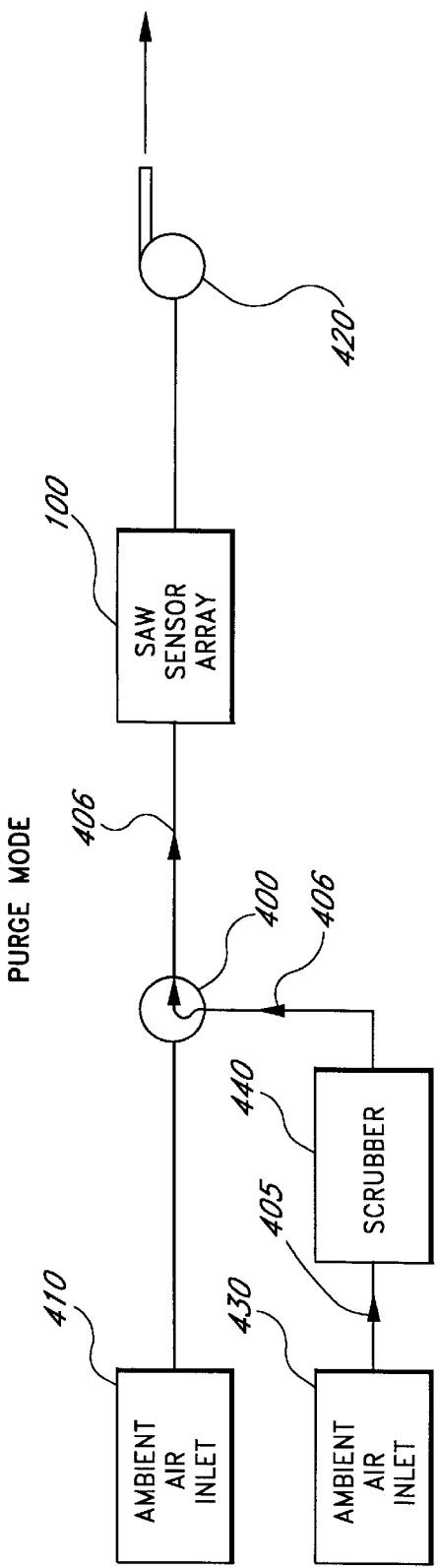

CHEMICAL SENSOR ARRAY

BACKGROUND OF THE INVENTION

The present invention relates generally to a real time contamination monitor, and more specifically, to an array of chemical sensors which is capable of measuring chemical contamination at the molecular level.

Environmental hazards are becoming more commonplace, with release of airborne chemicals often posing risks over a widespread area. Rapid and accurate detection of such chemicals is necessary to safeguard workers and the population at large. Chemical detectors for detecting at the molecular level commonly comprise polymer coated surface acoustic wave (SAW) sensors that detect, identify, and quantify the substance. A SAW sensor operates in effect as a microbalance through the de-tuning of the crystal's resonant frequency as mass is added to its surface. When a SAW sensor is used as part of an oscillator, changes in the characteristics of acoustic waves propagating through the SAW sensor may be used to determine the nature of one or more substances that has adsorbed onto the sensor.

While such chemical sensor arrays can be battery powered, and therefore portable, a significant amount of power is required to run the array of sensors. The power requirements necessitate frequent battery changes or recharging which impair the usefulness of such portable sensor arrays. Additionally, if the sensor array is miniaturized for enhanced portability, crosstalk can result between the individual sensors in the array. Such crosstalk can degrade the signal-to-noise ratio and affect the detection capability of the array. Sensor performance can also be adversely affected by poor impedance matching between the individual sensors and the drive electronics, as well as by circuitry that requires long stabilization times.

Accordingly, there is a need for a compact, real time, battery operated, low power, low noise, high stability, miniaturized chemical sensor array which can detect changes in mass due to molecular contamination on the order of $10^{-11}$ to $10^{-13}$ g-cm$^{-2}$ or less, and chemical concentrations in the parts per million to parts per trillion range.

SUMMARY OF THE INVENTION

According to one aspect of the invention, a sensor array for detecting chemical substances includes a plurality of chemical detection sensors, a plurality of driver circuits for driving the plurality of detection sensors, respectively, and a power multiplexer electrically coupled to the plurality of driver circuits, in which the power multiplexer receives power from a power supply. By way of example, the driver circuits may comprise oscillator circuits. The sensor array further includes a signal processing unit (SPU) electrically coupled to the plurality of driver circuits and to the multiplexer, in which the multiplexer is responsive to the SPU to electrically couple the plurality of driver circuits to the power supply according to a predetermined timing pattern such that less than all of the detection sensors are powered at any instant in time to substantially eliminate cross talk between adjacent circuits. In a preferred embodiment of the invention, the timing pattern is such that no more than one of the detection sensors is powered at any instant in time.

The SPU preferably comprises a reference sensor, a microprocessor, a reference driver circuit for driving the reference sensor, and a mixer, which mixes the output of the reference driver circuit with the output from at least one of the sensor driver circuits to provide a signal to the microprocessor, the signal being indicative of chemical loading on at least one of the detection sensors. The reference sensor and the detection sensors preferably comprise respective surface acoustic wave (SAW) devices. Each of the plurality of driver circuits preferably comprises an oscillator circuit in the form of an integrated circuit such as an application specific integrated circuit (ASIC). The detection sensors are joined to their respective driver circuits by electrical paths that extend through a circuit board and are preferably no longer than one inch, more preferably no longer than one half inch, and still more preferably no longer than one quarter inch.

Another aspect of the invention comprises a method of operating a sensor array to sense a chemical substance, in which the method includes exposing a plurality of SAW sensors to a gas which may contain the chemical substance, using a plurality of oscillator circuits to drive the plurality of SAW sensors, respectively, providing power to only one of the plurality of oscillating circuits at a time, and processing signals from the sensors to detect the chemical substance. The chemical substance may comprise, for example, particles in the form of a vapor or an aerosol. In a preferred embodiment, the method further includes purging or degassing the sensing surfaces of the SAW sensors by providing a flow of air through a scrubber material to provide a flow of clean air, and directing the flow of clean air across the sensing surfaces to permit the chemical substance to desorb from the surfaces into the clean air.

BRIEF DESCRIPTION OF THE DRAWINGS

FIGS. 4A and 4B are schematic representations showing the air flow path through the sensor device when the device is operated in the detection and purge modes, respectively.

DETAILED DESCRIPTION OF THE PREFERRED EMBODIMENT

The preferred embodiment of the present invention comprises a chemical detection unit having an array of individual sensors powered by a battery. Electrical power requirements are reduced by multiplexing the battery power to the individual sensors. In addition to reducing power requirements, the multiplexing also eliminates crosstalk between the individual sensors. Impedance matching between the sensors and the driver electronics is enhanced by the component layout.

Figure 1:
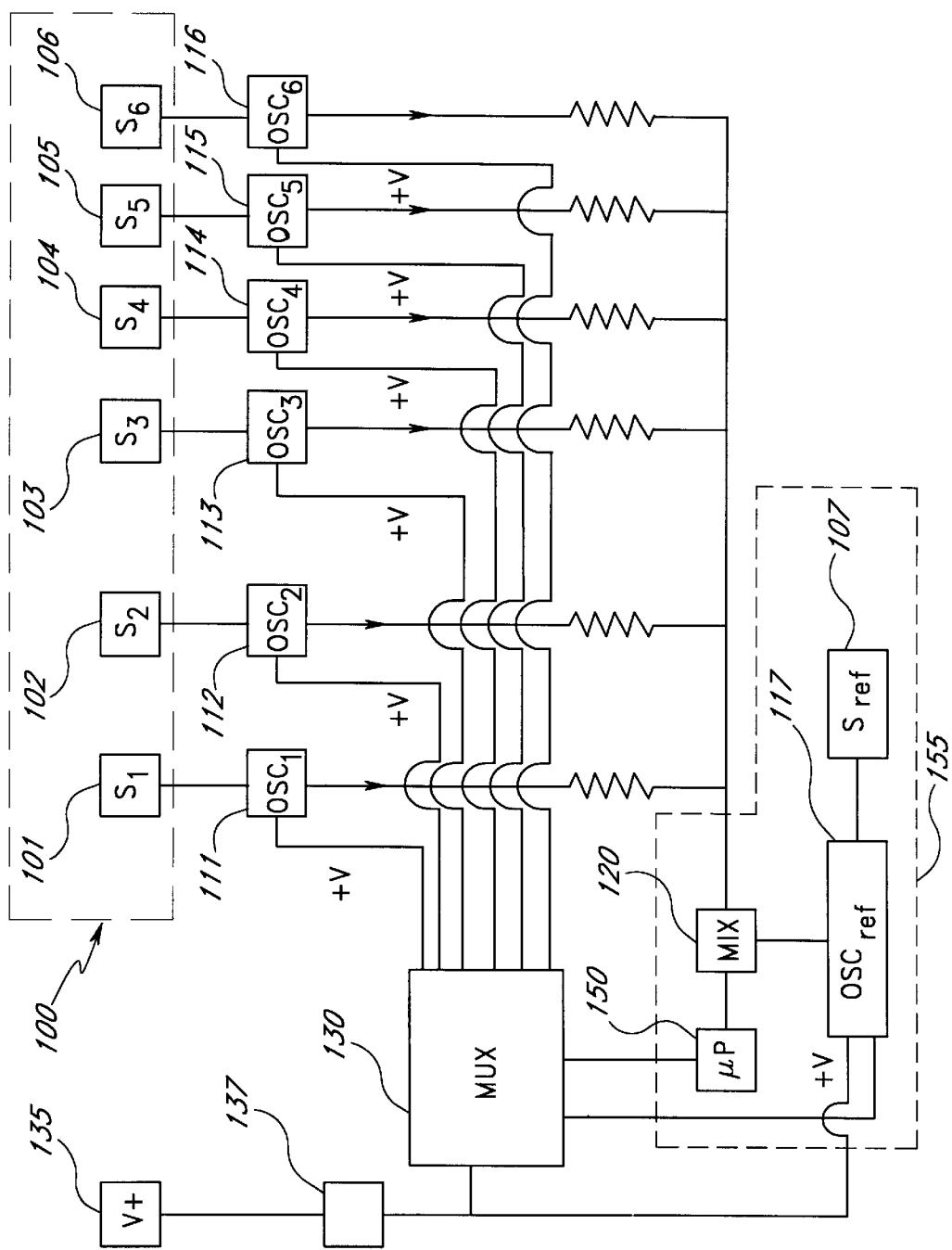
FIG. 1 is a schematic representation of a preferred embodiment of the invention, in which a plurality of chemical detection sensors are arranged in an array and power is multiplexed individually to the sensors.

As shown in FIG. 1, detection sensors comprised of surface acoustic wave (SAW) devices 101, 102, 103, 104, 105, 106, are arranged in an array 100 to detect the presence of chemical substances such as airborne trace contaminants. Preferably, the chemical substances to be detected comprise particles, such as molecules in the form of a gas vapor or an aerosol. While the preferred embodiment incorporates six SAW detection sensors 101–106, more or fewer detection sensors may be used. The operation and characteristics of SAW sensors are described in U.S. Pat. Nos. 5,645,608 to Lokshin et al., 5,476,002 to Bowers et al., 5,469,369 to Rose-Pehrsson et al., and 5,488,866 to Ravel et al., all of which are hereby incorporated by reference herein. Each SAW detection sensor 101–106 comprises a piezoelectric crystal, with the top few layers of the piezoelectric surface being driven to oscillate in a surface acoustic mode by a respective driving circuit such as an oscillator 111, 112, 113, 114, 115, 116. An electric field is applied parallel to the surface of the crystal, and Rayleigh waves are generated which move along the surface of the crystal. The resonant frequency of the crystal changes as a function of the mass of the trace contaminant adsorbed onto the crystal surface. The ability of the array to identify selected chemicals is enhanced by applying coatings to the sensing surfaces of the sensors 101–106, as is well known in the art. The coatings increase adsorption rates onto the surface of the SAW sensors 101–106. A different coating (or coatings) is preferably applied to each of the sensors 101–106, so that each SAW sensor has an affinity for a particular chemical or class of chemicals. The response of the SAW sensors 101–106 depends on the types and amounts of chemicals deposited on their respective sensory surfaces. Each mixture of chemicals will yield a unique response, and thus, detection of any particular mixture will provide an associated "fingerprint" which is indicative of that chemical substance.

In the preferred embodiment, identification of chemicals is accomplished using a signal processing unit 155, which includes a reference sensor 107, a mixer 120, a reference driving circuit 117, such as an oscillator and a microprocessor 150. The reference sensor 107 preferably comprises a SAW device that is connected to the oscillator circuit 117. The reference SAW 107 is covered so that it is shielded and sealed against the sample of air being sensed. In response to driving signals from the oscillator 117, the reference SAW 107 generates an output signal at its resonant frequency. Such output signal passes through the reference oscillator 117 to the mixer 120 which sequentially mixes such output signal with each of the respective outputs (resonant frequencies) from the detection sensors 101–106.

For any particular sensor 101–106, the signal from the mixer 120 is indicative of the particular chemical substance loaded onto (in general, absorbed onto) that sensor, and the characteristics (e.g., the beat or difference frequency) of this signal are analyzed by the microprocessor 150. By deconvolving the signal from the mixer 120 using various algorithms known in the art and correlating the results with known "fingerprints" particular to various chemicals, the identification and concentration of the chemicals adsorbed onto the surfaces of SAW sensors 101–106 can be determined.

Figure 2:
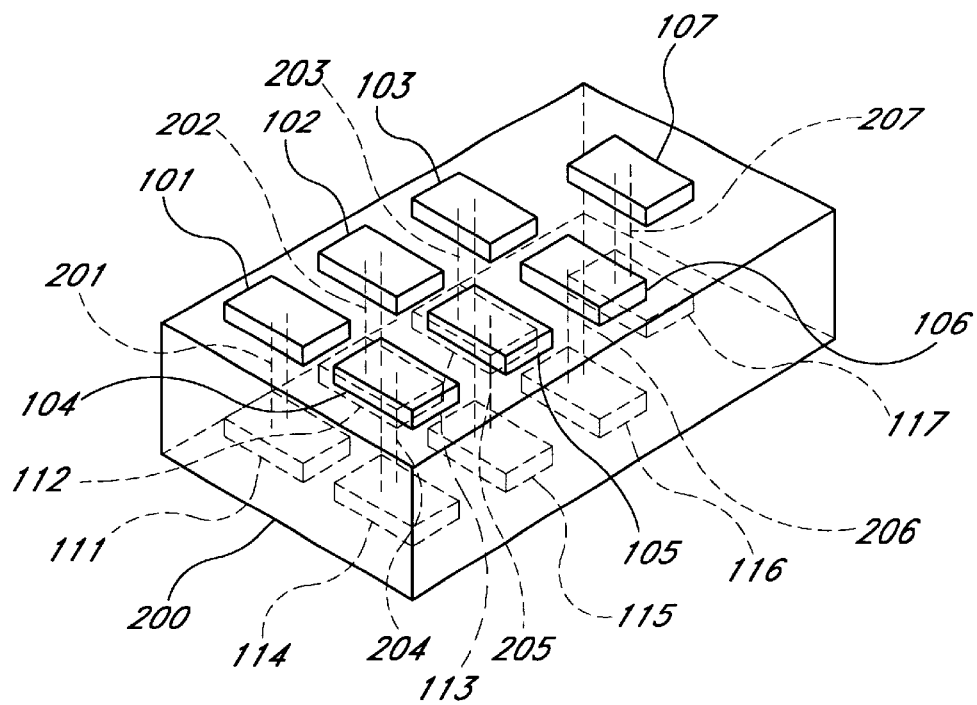
FIG. 2 shows the chemical detection sensors and the respective circuits that drive them located on opposite sides of a circuit board.
Figure 3:
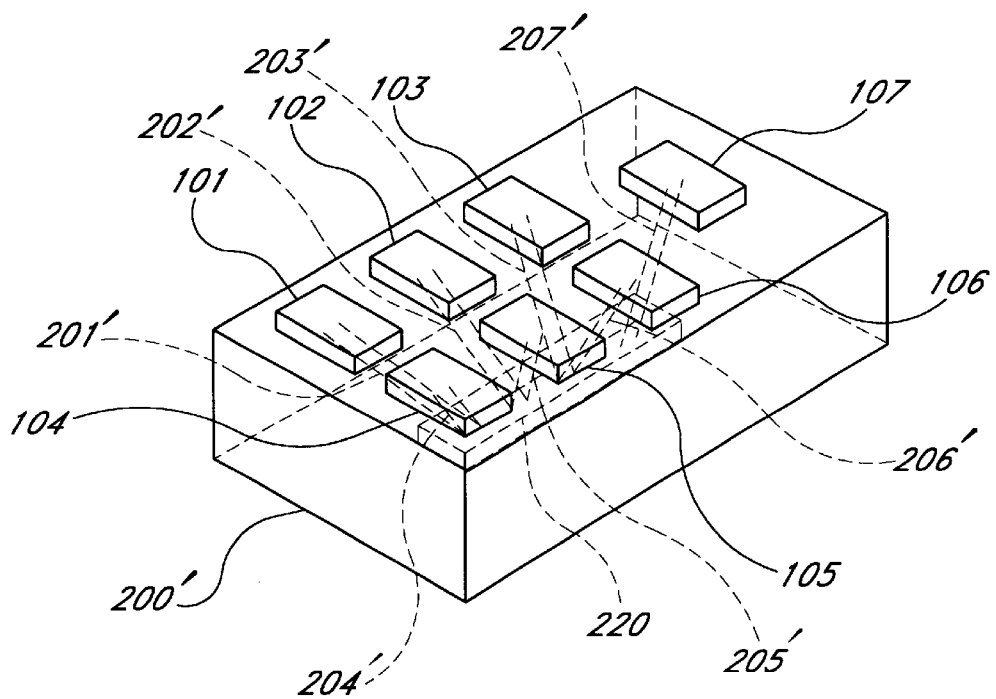
FIG. 3 shows a configuration similar to that of FIG. 2, except that the respective driving circuits are integrated into a single chip.

The sensor oscillators 111–117 are preferably comprised of individual application specific integrated circuits (ASICs) that incorporate impedance matching circuits. The ASICs also include amplifiers which amplify the signals output by the sensors 101–107. Although these ASICs are identical in the preferred embodiment, they may alternatively be individually designed and tailored for processing specific sensor responses. As shown in FIG. 2, the individual ASICs 111–116 for the sensors 101–106 may each comprise a separate chip, or alternatively, as shown in FIG. 3, the individual ASICs 111–116 may be integrated on a single chip. In either case, only one of the sensor ASICs 111–116 is dedicated to each of the SAW sensors 101–106.

Referring again to FIG. 1, power to the sensor oscillators 111–116 is controlled by a multiplexer 130, such as a digital switch, which sequentially applies voltage to each oscillator 111–116. Power is supplied to the multiplexer 130 by a power supply 135 which may be connected to the multiplexer via a power switch 137. The power supply preferably consists of one or more storage batteries such as alkaline batteries or lithium batteries. The mixer 120 and the multiplexer 130 are controlled by the microprocessor 150. In multiplexing power to the sensor ASICs 111–116, power is applied so that not all of the sensor ASICs 111–116 are powered at any instant in time. Preferably, the multiplexer 130 supplies power to the sensor ASICs 111–116 according to a predetermined timing pattern in which only one of the sensor ASICs 111–116 is powered at any instant in time. This ensures that there is no crosstalk between the sensor ASICs 111–116, thereby facilitating low noise operation of the device. In addition, by multiplexing power to the individual sensor ASICs 111–116, the overall power consumption is reduced. Power from the power supply 135 is preferably applied continuously to the reference ASIC 117. Alternatively, power may be distributed intermittently to the reference ASIC by the multiplexer 130 so that it is only on when one of the sensor ASICs 111–116 is on.

Use of the ASICs 111–116 also allows the microprocessor to rapidly interrogate each sensor 101–106 with low noise and high stability. Because the circuitry of each ASIC is integrated onto a common silicon substrate with short conductive paths, such circuitry does not require a long stabilization time and stabilizes quickly when power is applied, thereby enhancing system performance.

As shown in FIG. 2, the detection sensors 101–106 and the reference sensor 107 are mounted on one side of a circuit board 200, while the sensor ASICs 111–116 and the reference ASIC 117 are mounted on the opposite side of the board 200. The ASICs 111–117 are electrically coupled to their respective sensors 101–107 by respective electrical conductors 201–207 which extend through the board. The ASICs 111–117 and sensors 101–107 are arranged with each ASIC 111–117 directly opposite the sensor 101–107 that it drives, so that the length of each conductor 201–207 is approximately equal to the thickness of the board. The electrical conductors 201–207 provide respective electrical paths that are each preferably no longer than 1 inch, and more preferably no longer than one half inch, and still more preferably no longer than one quarter inch.

As mentioned above, the individual ASICs 111–117 can be embodied in respective separate chips as in FIG. 2, or such individual ASICs 111–117 can be embodied in fewer chips, such as the single chip shown in FIG. 3. The components discussed in FIG. 2 are shown in FIG. 3 with the corresponding referenced numbers primed. As in the embodiment of FIG. 2, the respective electrical paths 201'–207' of FIG. 3 which pass through the circuit board 200' are preferably no longer than 1 inch, and more preferably no longer than one half inch, and still more preferably no longer than one quarter inch.

The chemical substances to be detected are introduced into the device by drawing in ambient air containing the chemical substances to be detected. As illustrated in the schematic diagram of FIG. 4A, a three way valve 400 such as a magnetically latched solenoid valve is positioned in a detection mode to admit ambient air represented by arrow 405 through a first ambient air inlet 410 and onto the array 100 of detection sensors 101–106. Air is drawn past the sensor array 100 by a pump 420. As the air passes over the surfaces of the SAW sensors 101–106, the substances in the air to be detected are loaded (e.g., through absorption) onto the respective coated sensing surfaces of the detection sensors 101–106.

Alternatively, a gaseous sample may be obtained from a surface by utilizing a sample acquisition device such as that disclosed in the copending application of William D. Bowers, Ser. No. 09/151,743, filed on the same date as the present application, entitled "Pulsed Air Sampler," which is hereby incorporated herein by reference.

As soon as the response from the SAW sensors 101–106 is processed to detect the chemical substance in the air sample, the microprocessor 150 immediately switches the unit from a detection mode to a purge mode. Such immediate switching minimizes the loading on the polymer coated surfaces and allows the detection sensors 101–106 to be cleaned quickly, so that a new sample can be drawn in to confirm the results of the previous sample. The microprocessor automatically switches back and forth in this manner between detection mode and purge mode until the chemical substance is no longer detected (i.e. the ambient air is free of the substance).

To efficiently purge the detection sensors 101–106, a source of clean air is required, so that the adsorbed chemical remaining on the detection sensors 101–106 can be desorbed. Such clean air is created in the disclosed detection unit by drawing ambient air (which may contain the substance(s) to be detected) through a second ambient air inlet 430 which leads to a scrubber 440. The scrubber 440 contains charcoal or another substance, such as Tenax®, that absorbs, deactivates, or otherwise neutralizes chemicals from ambient air. Suction for drawing the air through the scrubber is provided by activating the pump 420 and positioning the three way valve 400 so that air from the scrubber 440 is admitted into the sensor array 100. The stream of clean, purified air 406 from the scrubber is thus drawn past the sensor array 100, thereby allowing the chemicals loaded onto the array to desorb into the clean air. After the sensor array 100 has been purged in this manner for typically 1–3 minutes, the chemical which had been adsorbed onto the sensors 101–106 will be sufficiently desorbed back into the stream of clean air 406 that another sample of unpurified ambient air can be admitted through the air inlet 410 to the sensor array 100 for analysis.

The invention may be embodied in other specific forms without departing from its spirit or essential characteristics. The described embodiments are to be considered in all respects only as illustrative and not restrictive. The scope of the invention is therefore indicated by the appended claims rather than by the foregoing description. All changes which come within the meaning and range of equivalency of the claims are to be embraced within that scope.

What is claimed is:

1. A sensor array for detecting chemical substances, comprising:
   a plurality of chemical detection sensors;
   a plurality of driver circuits for driving said plurality of detection sensors, respectively;
   a power multiplexer electrically coupled to said plurality of driver circuits, said power multiplexer receiving power from a power supply; and
   a signal processing unit (SPU) electrically coupled to said plurality of driver circuits and to said multiplexer, said multiplexer responsive to said SPU to electrically couple said plurality of driver circuits to the power supply according to a predetermined timing pattern such that less than all of said detection sensors are powered at any instant in time to substantially eliminate cross talk between adjacent driver circuits.

2. The sensor array of claim 1, wherein said multiplexer comprises a digital switch.

3. The sensor array of claim 1, wherein said timing pattern is such that no more than one of said detection sensors is powered at any instant in time.

4. The sensor array of claim 1, wherein said SPU comprises a reference sensor, a microprocessor, a reference driver circuit for driving said reference sensor, and a mixer, said mixer mixing an output of said reference driver circuit with an output from at least one of said sensor driver circuits to provide a signal to said microprocessor, wherein the signal is indicative of chemical loading on at least one of said detection sensors.

5. The sensor array of claim 1, wherein each of said driver circuits comprises an oscillator circuit in the form of an integrated circuit; and
   wherein said reference sensor and said detection sensors comprise respective SAW devices.

6. The sensor array of claim 5, wherein each of said integrated circuits comprises an ASIC.

7. The sensor array of claim 6, wherein each of said ASICs is a separate, individual chip.

8. The sensor array of claim 6, wherein all of said ASICs are integrated on a single chip.

9. The sensor array of claim 1, further comprising a power supply comprising one or more storage batteries.

10. The sensor array of claim 9, wherein said one or more storage batteries comprises at least one lithium battery.

11. The sensor array of claim 1, wherein said detection sensors are mounted on one side of a circuit board, said plurality of driver circuits comprise at least one integrated circuit disposed on an opposite side of said board, and said detection sensors are electrically coupled to a plurality of respective driver circuits by respective electrical paths.

12. The sensor array of claim 11, wherein said electrical paths extend through said board.

13. The sensor array of claim 11, wherein said electrical paths are no longer than one inch.

14. The sensor array of claim 11, wherein said electrical paths are no longer than one half inch.

15. The sensor array of claim 11, wherein said electrical paths are no longer than one quarter inch.

16. A method of operating a sensor array to sense a chemical substance, said method comprising:

exposing a plurality of SAW sensors to a gas which may contain the chemical substance;

using a plurality of oscillating circuits to drive the plurality of SAW sensors, respectively;

providing electrical power to only one of the plurality of oscillating circuits at a time to substantially eliminate cross talk between adjacent oscillating circuits; and processing signals from the sensors to detect the chemical substance.

17. The method of claim 16, wherein the chemical substance comprises particles.

18. The method of claim 16, wherein the chemical substances in the form of an aerosol.

19. The method of claim 16, additionally comprising providing power from the oscillating circuits to the SAW sensors along an electrical path that is no more than about one quarter inch in length.

20. The method of claim 16, wherein said exposing comprises providing a flow of gas containing the chemical substance across respective sensing surfaces of the SAW sensors to load the sensing surfaces with the chemical substance.

21. The method of claim 20, wherein the gas comprises air.

22. The method of claim 21, additionally comprising scrubbing the sensing surfaces of the SAW sensors by providing a flow of air through a scrubber material to provide a flow of clean air, and directing the flow of clean air across the sensing surfaces to permit the chemical substance to desorb from the surfaces into the clean air.

23. The method of claim 16, comprising comparing respective outputs from the SAW sensors with an output from a reference SAW sensor.

* * * * *